(12) United States Patent
Lauglin

(10) Patent No.: US 7,183,115 B1
(45) Date of Patent: Feb. 27, 2007

(54) GAS SAMPLE ANALYSIS SYSTEM

(75) Inventor: Robert M. Lauglin, Miramar, FL (US)

(73) Assignee: Lawrence Factor, Inc., Miami Lakes, FL (US)

( * ) Notice: Subject to any disclaimer, the term of this patent is extended or adjusted under 35 U.S.C. 154(b) by 320 days.

(21) Appl. No.: 10/045,229

(22) Filed: Nov. 9, 2001

(51) Int. Cl.
*G01N 31/00* (2006.01)

(52) U.S. Cl. .............................. 436/38; 422/83; 436/60; 73/31.02; 702/24

(58) Field of Classification Search .................. 422/83; 436/38, 60, 181; 702/22, 23, 24, 30; 73/31.01–31.03
See application file for complete search history.

(56) References Cited

U.S. PATENT DOCUMENTS

| | | | |
|---|---|---|---|
| 5,521,845 A * | 5/1996 | Ukon et al. | 702/33 |
| 5,835,871 A * | 11/1998 | Smith et al. | 701/29 |
| 6,033,457 A * | 3/2000 | Lawless | 95/4 |
| 6,466,133 B1 * | 10/2002 | Skardon | 340/627 |
| 6,604,033 B1 * | 8/2003 | Banet et al. | 701/33 |
| 6,606,566 B1 * | 8/2003 | Sunshine | 702/22 |
| 6,631,333 B1 * | 10/2003 | Lewis et al. | 702/24 |
| 2002/0152037 A1 * | 10/2002 | Sunshine et al. | 702/23 |
| 2003/0216869 A1 * | 11/2003 | Sunshine | 702/22 |

OTHER PUBLICATIONS

Richard W. Walker, "Nevada gets new emissions data system," Government Computer News, Jul. 1997 at http://www.gcn.com/archives/sl/1997/July/cov1.htm (copyright 1999 by Post-Newsweek Business Information, Inc.).*

* cited by examiner

*Primary Examiner*—Jan M. Ludlow
(74) *Attorney, Agent, or Firm*—Malin, Haley & DiMaggio, P.A.

(57) ABSTRACT

A gas analyzer system for analyzing samples of compressed or ambient gas such as breathing air within a scuba tank, SCBA or ambient air within an industrial plant and informing the user as to the results of the sample's gas purity without the gas sample having to be physically transported to an accredited laboratory. The system comprises a gas analyzer situated at a user facility for receiving the contents of a gas sample and detecting gas purity characteristics, and a server situated at a remote certified testing site and electrically coupled to the gas analysis module via data transmission, such as a wireless or a computer network connection, wherein the server, maintained by a qualified third party receives and stores the gas purity characteristics in the form of computer-readable data signals. Computer instructions stored within the qualification server compares the computer-readable data signals representing gas purity characteristics with the contents of a database containing threshold gas purity parameters. After determining if the gas sample characteristics for that particular gas sample meet the required threshold limits, the user receives immediate notification, either by e-mail or by receipt of a fax at the user site, informing the user whether the given gas sample has achieved the required gas purity levels by a qualified third party.

5 Claims, 2 Drawing Sheets

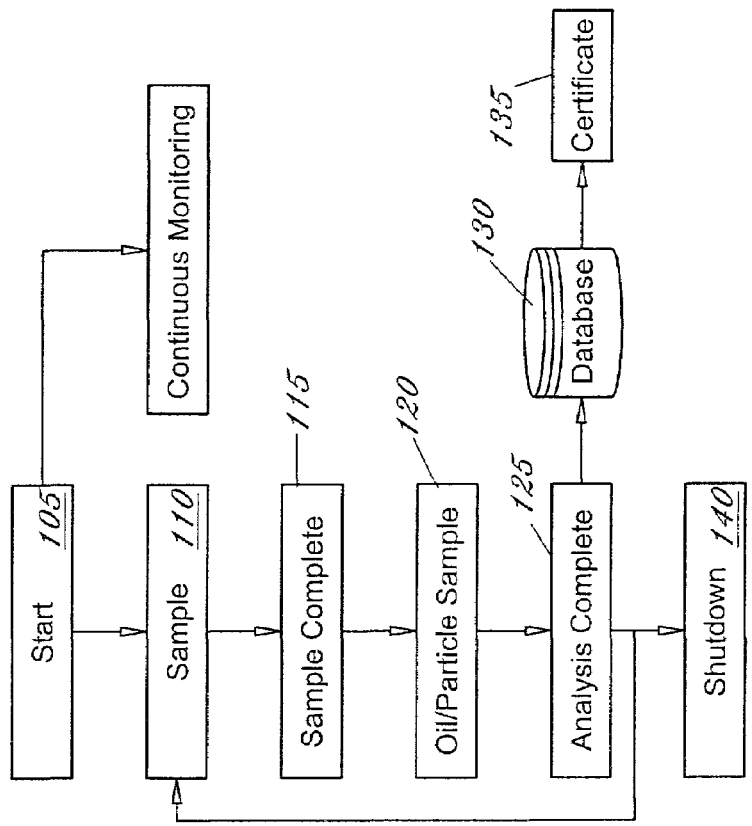
Fig. 4
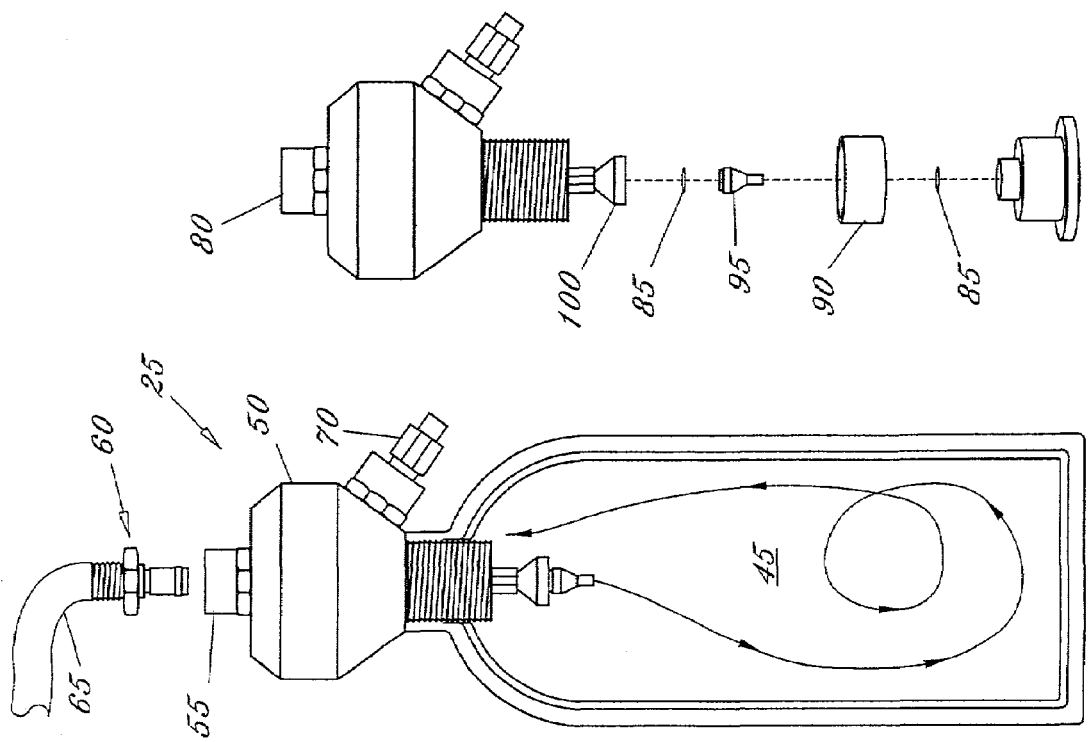
Fig. 3
Fig. 2

GAS SAMPLE ANALYSIS SYSTEM

BACKGROUND OF THE INVENTION

1. Field of the Invention

The invention generally relates to a gas purity analysis system, and particularly to a portable system capable of analyzing a gas sample at a user facility and transmitting gas purity and/or oil and particle information to a remote site where it is quickly determined if the gas substance has passed certain gas purity requirements.

2. Description of the Prior Art

There is a growing need in the industry for gas purity testing systems that can provide gas purity analysis results to the user quickly and efficiently. The standard method in the art for testing the quality of gas samples is to first capture the sample and then transport the actual sample to a certified, accredited laboratory for analysis. The user must then wait, weeks perhaps, until the sample has been analyzed and certified by a qualified government laboratory.

However, given the demand for quality air sources, such as compressed air tanks for SCUBA diving, and compressed air used for human inhalation in industrial plants, hospital and by firemen, as well as ambient air, the standard method is not practical. It is cumbersome and costly, given the potential loss of sales a vendor may experience waiting for certification of the gas sample. These samples often must be taken periodically at short time intervals exacerbating the problem.

Further, a gas sample that passes the required gas purity standards and obtains certification one day may, if impurities enter the tank or facility, become tainted and fall below the certification requirement the next day. However, given the length of time and cumbersome nature of transporting gas sample to a test center, the facility, possibly a hospital, will rely on its prior certification, leading to a possibly dangerous, if not life-threatening situation wherein air, believed to be pure based upon a prior, three-week-old test, actually contains impurities.

Accordingly, what is needed in the art is a gas purity sample analysis system that allows a user to effectively test an air sample on site as often as the user would like and without the actual sample being physically carried to a testing facility, while still being certified by a qualified third party, by inserting the gas sample into a sampling unit located at the user's facility, and the results being electrically transmitted remotely to the certification facility. The gas purity and/or oil/particle content information is then sent, via electronic data transmission, to a monitoring center where the sample quality information is compared by qualified people to a database of industry standards, and the user is notified, within minutes, if the sample tested has attained certification by meeting or exceeding industry purity standards.

It is, therefore, to the effective resolution of the aforementioned problems and shortcomings of the prior art that the present invention is directed.

SUMMARY OF THE INVENTION

The present invention provides a gas sample quality analysis system for analyzing and certifying samples of breathing air substances comprising a gas analysis module situated on site at a user facility for capturing a real time sample of a gas, for analyzing and detecting gas purity characteristics of the sample and for converting the gas purity characteristics into computer-readable data, said data representative of the gas purity characteristics for a particular sample, and a computer server situated at a gas certification site and electrically coupled to the gas analysis module, the server adapted to receive the computer-readable data via data transmission, the server containing a data storage component for identifying the sample being tested and for storing the gas purity characteristics, and computer instructions capable of determining if the gas sample passes certain gas purity requirements. The data transmission system may be any form of data transmission including but not limited to both hard-wired and wireless, and, preferably is accomplished via a computer Internet connection. The data analysis site must be a government-approved facility that is qualified to certify the quality of air samples.

In one embodiment of the present invention, the gas analysis apparatus further comprises a data certification component for informing a user if the gas sample has passed the gas purity requirements. This could be in the form of an electronic or printed message. In another embodiment, test results are stored and/or printed at a qualified monitoring center, which is an accredited gas purity testing laboratory, or at another location. If the samples are acceptable, the air quality is certified and the user notified electronically.

The gas analysis module comprises an air collection container for collecting and temporarily storing the gas sample, an UV or ionic gas analyzer for detecting gas impurities in the gas sample, and data processing CPU for converting the detected gas impurity data into computer-readable data, the digital data representing gas impurity characteristics of the gas sample.

The present invention is also a method of analyzing a gas sample without the necessity of transporting the gas sample to a qualified remote certification testing facility. The method comprises the steps of capturing a real time gas sample within a container for use in a gas analyzer situated at the user facility, determining and measuring gas purity characteristics of the gas sample, converting the gas purity characteristics into computer readable data, and transmitting the computer readable data representing the gas purity characteristics from the user facility to a server situated at a qualified certification site that is electrically coupled to the gas analyzer containing the sample. The server located at the certification site can receive the computer readable data via data transmission means, the server containing a data storage element for storing the computer readable data and computer instructions capable of identifying the user, measuring the date and time of the sample and determining if the gas sample passes certain gas purity requirements.

After the gas sample has been tested for gas purity, the sample can then be tested for oil particle content via the same apparatus and methods as described above.

To utilize the present invention, a user installs a gas analyzer at the user site. Depending upon the type of air to be analyzed (compressed or ambient), an appropriate gas analyzer module is installed at the user's site. The user first inserts the gas sample into a gas sample storage tank, via an air hose. The user then notifies a representative at a remote air sample certification center that the user needs to test a gas sample. This is usually accomplished by the user simply activating the computer connected to the gas analyzer. The representative at the monitoring center initializes the user's gas analyzer remotely and informs the user that the module is ready to analyze samples. The user's facility may be a dive shop with SCUBA equipment, a hospital or fire station, or a large industrial plant containing ambient or compressed air that needs to be analyzed and certified as safe. The sample to be tested could be compressed air in a SCUBA tank, or a sample of ambient air.

After the system has been initialized, the gas sample stored in the air tank is transferred to a gas sample analysis tank, where it is analyzed for gas purity via a series of detection probes. Gas purity information is converted to computer-readable data by computer instructions stored within a computer located within the gas analyzer. A digital stream of data corresponding to the gas purity characteristics of the gas sample is transmitted to a remote monitoring center, where it is stored on a server. The method of transmission may vary, and it is within the spirit of the invention to employ any form of electronic data transmission common in the art in order to transmit the information accurately and quickly. An intranet or Internet connection can be established between the computer within the gas analysis module at the user site and the server at the monitoring center. Other forms of wireless transmission could also be utilized.

Upon receipt of the data stream containing the information about the analyzed gas sample, the server controlled by the certification center stores this information and compares the data to the contents of a reference database containing gas purity threshold parameters. If the user's gas sample meets the threshold parameters, then the gas sample has passed its test by the certification center and the user is notified. This notification could be in the form of a return e-mail or fax, which is automatically forwarded to the user. Conversely, if the gas sample characteristics do not meet the required stored threshold parameters, a message will be transmitted to the user, informing the user of the negative result. The results of the test are archived and, if desired, printed.

In either case, the user, without having to transport the sample to an accredited facility or laboratory, is informed, usually within minutes, as to the success or failure of the gas purity test, performed by a certified testing center.

In a further embodiment of the present invention, after the gas sample has been analyzed for gas purity levels, or in lieu of detecting the gas purity, the air sample can be analyzed for oil particle content. To accomplish this, the user removes the oil/particle accessory unit from the particulate analyzer, attaches the unit to the air storage tank and places an oil sample within the filter portion of the oil/particle accessory unit. The filter optically detects oil particles in the gas sample. The oil particle data is processed and transmitted to the remote monitoring center in the same means as described above. Again, the user can be notified as to the results of the oil purity test by the certifying center.

It is therefore an object of the invention to provide a gas analyzer system that eliminates the need for a user to physically transport a gas sample to a certification facility for gas purity testing.

It is another object of the invention to provide a gas analyzer system that reports to the user the success or failure of the gas purity test within minutes by a third party, certified, qualified entity approved by the government.

It is yet another object of the invention to provide a gas analyzer system that provides the user with a printed and/or electronic message informing the user of the success or failure of the gas purity test.

It is still another object of the invention to provide a gas analyzer system that detects the existence of oil particle impurities within the gas sample and can get remote certification as to the particulates.

In accordance with these and other objects which will become apparent hereinafter, the instant invention will now be described with particular reference to the accompanying drawings.

BRIEF DESCRIPTION OF THE DRAWINGS

FIG. 2 is an illustration of the air collection tank used in the present invention.

FIG. 3 is an illustration of the oil and particle accessory unit used in the present invention.

FIG. 4 is a flowchart representing the steps performed by the gas sample analyzing system of the present invention.

DESCRIPTION OF THE PREFERRED EMBODIMENTS

Figure 1:
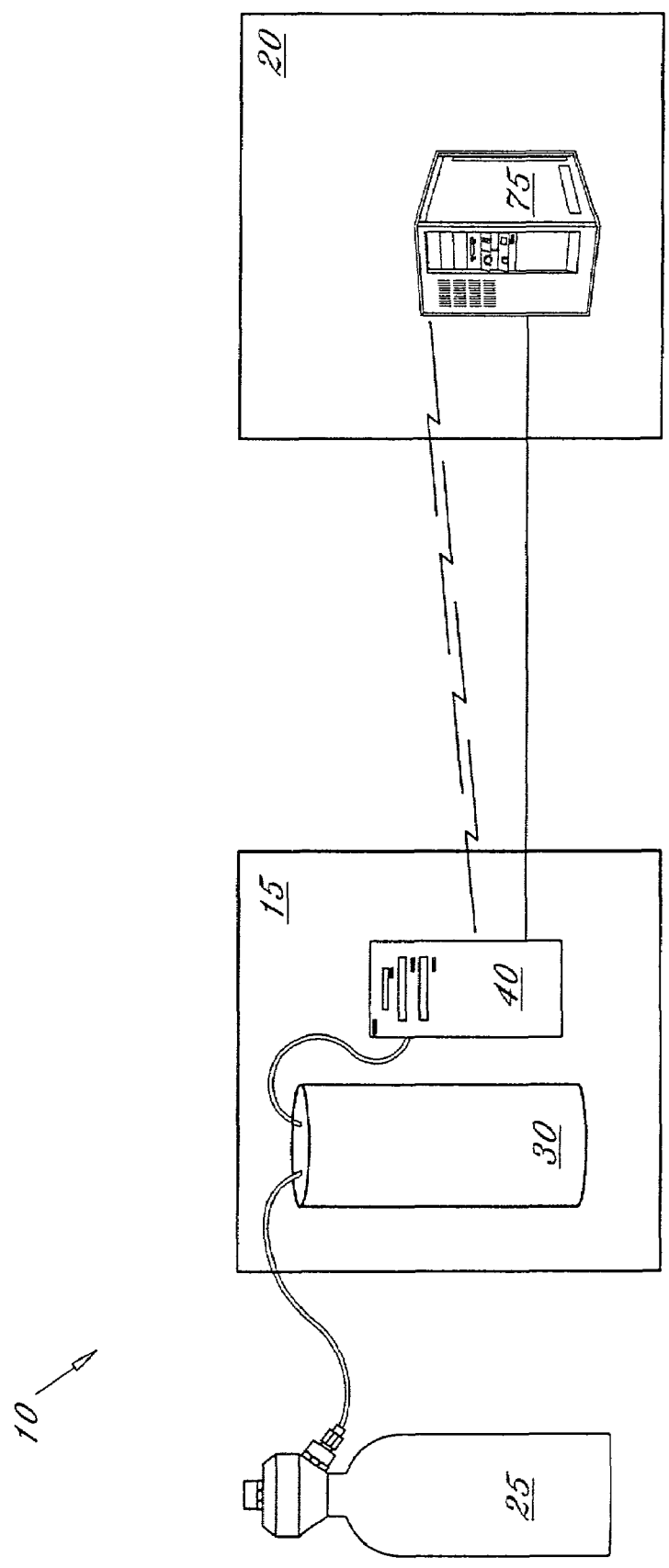
FIG. 1 is an illustration of the components of the gas sample analyzing system of the present invention.

In a preferred embodiment of the present invention, an improved machine is provided that allows a user to test and receive third party certification of an air sample for both gas and oil impurities without having to physically transfer the real time gas sample to a certified remote facility.

Referring to FIG. 1, the gas analyzer system of the present invention 10, can be seen. The system is comprised of a gas analyzer module 15, located at the user's facility, and a data monitoring center 20 located at a facility that has the governmental power to certify gas quality as a third party.

Gas analyzer module 15 is comprised of a gas analysis tank 30 having a gas impurity detector and a computer 40 having a data storage component and a data processor.

Air collection tank 25 containing the sample to be analyzed is connected to gas analysis tank 30. Air collection tank 25 could be any air storage tank, or, preferably, the type illustrated in FIG. 2. Information transmitted between module 15 and monitoring center 20 can be via a wired connection, such as the Internet or an intranet, or via wireless RF communication means.

In the preferred embodiment, shown in FIG. 2, air collection tank 25 includes an air compartment 45 containing the captured gas sample, manifold 50, an air intake port 55 to receive the air sample via a connection hose 65 having an adapter 60 threaded to one end of hose 65. Adapter 60 is joined to one end of hose 65 which is connected at its other end to the user's air source.

Once the gas sample has entered air collection compartment 45, the user turns off the air source and activates computer 40. Upon activation, a signal is sent to a representative at remote monitoring center 20, qualified as a third party that can certify the quality of the sample. Without a third party certification, the user cannot provide products safely to customers. There, the qualified representative receives the signal, indicating that a user at a specific location has activated computer 40 of gas analyzer module 15. The system is now ready to receive and analyze the gas sample. A portion of the gas sample exits the air collection tank 45, where the sample had been temporarily stored, via a sample out/relief port 70, and enters gas sample analysis tank 30. Within tank 30, are gas purity detectors which detect and analyze the contents of the gas sample.

The system can be calibrated to detect virtually any type of gas impurity. The following is a non-exhaustive list of gas impurities the present inventions capable of detecting. This list is illustrative only and is set forth here merely to give a broad understanding of the some of the impurities recognized:

| Analytes | Range |
| --- | --- |
| Carbon Dioxide | 0–100 ppm |
| Carbon Monoxide | 0–20 ppm |
| Hydrocarbons | 0–25 ppm |
| Water Vapor | 1–422 ppm |
| Nitric Oxide | 0–2.5 ppm |
| Sulfur Dioxide | 0–5 ppm |
| Halogenated Solvents | 0–10 ppm |
| Acetlylene | 0–.05 ppm |
| Halogenated Hydrocarbons | 0–5 ppm |
| Oil and Particles | 0–5 mg/m$^3$ |
| Oxygen | 0–37% |
| Nitrogen Dioxide | 0–2.5 ppm |
| Odor | None–strong |

Once the gas sample has been identified, analyzed and levels of gas impurities, if any, have been determined, this data is converted into digital signals by computer readable instructions in computer 40 and transmitted to the qualified, remote monitoring center 20 for certification. The means of data transmission can include virtually any form of data transmission including both hard-wired and wireless forms of transmission including a standard Internet connection. In the preferred embodiment, a standard computer network connection, via a 56K modem connection is used. Typically, the gas purity information for a single gas sample takes up about 11 KB of computer storage space.

Once the transmission of the data has been complete, the user is notified that the sample has been successfully transmitted.

A qualified representative at the remote monitoring center receives the sample data, and the sample data stored on a computer server 75. The data is compared to known preexisting list of gas impurity threshold values to determine if a specific gas impurity level has been exceeded. The results of the comparison test are then determined, the information stored under the name of the user, and the test results sent back to the user, either by an electronic message, or via a fax or paper delivery. A certificate showing compliance with various gas purity standards is transmitted.

Upon completion of the gas phase, the user may also which to have the gas sample checked for the existence of oil particles.

FIG. 3 refers to the oil/particle accessory unit 80 of the present invention. To check for the existence of oil/particles in the previously tested gas sample, the user must first remove the gas purity attachments used during the gas phase of the test and then remove the filter assembly 95 and 100, which contains the filter element 85. Filter element 85 is then removed and reinserted in oil/particle accessory unit 80 and is enclosed within the lens cap 90 as shown in FIG. 3. Oil/particle accessory unit 80 is then inserted into the analyzer. As with the gas phase, the system will notify the user, either via a voice message from the computer's speaker, or via an electronic or written message or signal, that the oil particle information has been transmitted to the certified monitoring center 20. Once again, the method of data transmission can be in any number of forms including hard wired or wireless and Internet connections.

In the preferred embodiment of the invention, both the gas purity and the oil particle data is automatically transmitted from the gas analyzer module at the user's site to the certified monitoring center 20 via a standard Internet connection (DSL, cable, 56K modem, for example), after each phase of the test has been concluded. In an alternate embodiment, the computer provides an indication to the user that the test has been completed and the user can then notify a representative at monitoring center 20 that the test has been concluded and that the data should be transmitted. The data is then examined at the remote qualification site and compared with the database of acceptable standards. The user is then promptly notified as to the test results. The test results are archived and/or printed at monitoring center 20. Alternately, the results could be stored and/or printed at another location.

Referring now to FIG. 4, a flowchart is shown illustrating the steps taken to accomplish the present invention. After filling tank 25 with the air sample, the user initiates gas analyzer module 10 by activating module 15 located at the user's facility via step 105. The user accomplishes this step by depressing a button or switch on module 15, thus activating computer 40 and establishing a communication link back to monitoring qualification center 20. Upon activation of gas analyzer module 15, the computer within gas analyzer module 15 sends a signal to server 75 at the remote monitoring facility. Server 75 now awaits input from gas analyzer module 15.

The user is then prompted to enter the gas sample, step 110. The gas sample is analyzed for gas purity characteristics. Gas purity characteristics, in the form of computer-readable data is transmitted to remote facility 20 where it is stored on server 75. Remote facility 20, preferably, is a certified laboratory certified in ambient and compressed air purity testing. The data is compared with a database of gas purity standards and the test results are stored under the user's name and location. Preferably, server 75 forwards the certified test results to the user, or queries the user whether further gas samples are forthcoming. Alternately, the test results are not sent to the user until requested or until the oil particle portion of the test has been completed. The system, upon completion of the analysis, informs the user that the gas phase of the testing has been completed, via step 115.

If the user chooses to continue testing the gas sample for oil particle purity, the user is prompted to insert the oil/particle sample, step 120. The user removes the oil and particle accessory unit 80 from module 15. The same process takes place as described above for gas purity analysis. Upon completion of the test(s), an accredited certificate is printed out either at remote center 20, or at a different location, and the test results for that particular gas sample archived in a database, via steps 125 through 135. The user is notified either by e-mail, fax or mail as to the results of the test. In this fashion, a user may have test results within minutes. The user can keep reinserting samples. If no more tests are desired, the system is shutdown via the remote facility, step 140.

The present invention provides expedited gas analysis where the sample is gathered and kept at the user site, is tested at the user site and is certified for safety remotely by qualified gas analysis experts without having to physically transport the actual gas sample from the user site to a qualified laboratory.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A method of analyzing a human breathing air sample derived from a user air source in order to determine the user air source air sample purity without the necessity of transporting the breathing air sample to a remote qualified third party breathing air testing facility and determining if the air sample passes the human breathing air purity standards, the method comprising the steps of:

provide a user air source for generating compressed human breathing air, said user air source used to supply SCUBA tanks and emergency air tanks at a user facility;

providing a human breathing air collection tank at said user facility;

collecting an air sample from said user air source in said air collection tank at said user facility;

collecting said breathing air sample within a breathing air analysis module from said air collection tank at said user facility;

determining breathing air purity characteristics of said human breathing air sample received within said breathing air analysis module from said air collection tank at said user facility;

converting said breathing air purity characteristics into computer readable data;

transmitting through an on-line computer network said computer readable data representing the air purity characteristics of said breathing air sample from said user air source at said user facility to a qualified server for certification of use situated at a remote site and electrically coupled to said breathing air analysis module, said server maintained by a qualified third party air purity certification site including a receiver for receiving said computer readable data via a data transmitter, said server containing a data storage element for storing said computer readable data;

determining if said breathing air sample passes certain gas purity requirements; and informing said breathing air user facility having said user air source if said breathing air sample has passed said breathing air purity requirements using an on-line response to a computer located at said breathing air producer user facility.

2. The method of claim 1, wherein said data transmission is via a wireless transmission.

3. The method of claim 1, wherein said remote site is an accredited breathing air purity testing facility.

4. The method of claim 1, further comprising the steps of storing and printing results of said breathing air sample analysis.

5. The method of claim 1, further comprising the step of comparing said computer-readable data related to said breathing air purity characteristics to a stored set of predetermined breathing air purity standards.

* * * * *